United States Patent
Benderly et al.

(10) Patent No.: US 7,528,278 B2
(45) Date of Patent: May 5, 2009

(54) TRANSESTERIFICATION PROCESS FOR PRODUCTION OF (METH)ACRYLATE ESTER MONOMERS

(75) Inventors: Abraham Benderly, Elkins Park, PA (US); Michael R. Ryan, Ridley Park, PA (US); Donald R. Weyler, Levittown, PA (US)

(73) Assignee: Rohm and Haas Company, Philadelphia, PA (US)

( * ) Notice: Subject to any disclaimer, the term of this patent is extended or adjusted under 35 U.S.C. 154(b) by 128 days.

(21) Appl. No.: 11/810,654

(22) Filed: Jun. 6, 2007

(65) Prior Publication Data

US 2007/0287841 A1 Dec. 13, 2007

Related U.S. Application Data

(60) Provisional application No. 60/813,070, filed on Jun. 13, 2006.

(51) Int. Cl.
 *C07C 67/02* (2006.01)
(52) U.S. Cl. .................................................... 560/217
(58) Field of Classification Search ...................... None
 See application file for complete search history.

(56) References Cited

U.S. PATENT DOCUMENTS

| 4,745,213 A | * | 5/1988 | Schlosser et al. ............ 560/217 |
| 5,027,027 A | | 6/1991 | Orbach et al. |
| 6,515,138 B2 | * | 2/2003 | Weir et al. ................ 548/324.1 |

FOREIGN PATENT DOCUMENTS

JP 2000-095731 A1 * 4/2000

* cited by examiner

*Primary Examiner*—Paul A Zucker
(74) *Attorney, Agent, or Firm*—Tifani Cottingham

(57) ABSTRACT

This invention utilizes a mixed salt transesterification catalyst in a transesterification process for the production of esters of alkyl(meth)acrylate monomers.

9 Claims, No Drawings

TRANSESTERIFICATION PROCESS FOR PRODUCTION OF (METH)ACRYLATE ESTER MONOMERS

This application claims the benefit of priority under 35 U.S.C. §119(e) of U.S. Provisional Patent Application No. 60/813,070 filed on Jun. 13, 2006.

The present invention relates to a transesterification process for the production of (meth)acrylate ester monomers from alkyl(meth)acrylates and alcohols. More particularly, the present invention is an improved transesterification process which involves addition of a transesterification mixed salt catalyst during the period of reaction.

As used herein, the use of the term "(meth)" followed by another term such as acrylate refers to both acrylates and methacrylates. For example, the term "(meth)acrylate" refers to either acrylate or methacrylate; the term "(meth)acrylic" refers to either acrylic or methacrylic; the term "(meth)acrylic acid" refers to either acrylic acid or methacrylic acid.

Esters of (meth)acrylates may be formed by transesterification of an alkyl (meth)acrylate with a selected alcohol, in the presence of a transesterification catalyst, followed by the elimination of a low boiling by-product alcohol in the form of an azeotrope with the alkyl(meth)acrylate.

More particularly, traditional transesterification processes involve feeding all of the reactants into a reactor and dehydrating the resulting reaction mixture by azeotropic distillation. Once the residual water level is acceptable, a suitable transesterification catalyst is added to the reaction mixture, and the mixture is heated to commence the transesterification reaction. The reaction products typically include the desired (meth)acrylate ester and a low boiling by-product alcohol. Azeotropic distillation is conducted to separate and remove the alcohol by-product, along with some of the starting alkyl (meth)acrylate. The temperature of the reaction mixture rises as the alcohol by-product is removed. Because the transesterification process is reversible, the rate of reaction is largely determined by rate of removal of the by-product alcohol.

Tin-based transesterification catalysts, such as dibutyl tin oxide (DBTO) and dibutyl tin dimethoxide, have been used in transesterification processes to produce esters of (meth)acrylates. Due to environmental concerns, tin-based catalysts were replaced by other more environmentally friendly catalysts, such as, for example, alkali metals and alkali metal hydroxides, such as lithium and lithium hydroxide such as the type disclosed in U.S. Pat. No. 5,072,027; however when compared to the tin-based transesterification catalysts the alkali metals and alkali metal hydroxide catalysts do not demonstrate the same level of chemical reactivity and selectivity. Furthermore, the alkali metals and alkali metal hydroxide catalysts require maximum dehydration before adding the catalyst. The catalyst fails to perform when substantial amounts of water exist in the reaction mixture. Moreover it is often the case that reactions employing alkali metals and alkali metal hydroxide catalysts require the addition of more than one charge of catalyst.

Thus what is needed is an improved transesterification process that makes use of an environmentally acceptable catalyst with the performance characteristics of DBTO, but is a (meth)acrylate ester monomer catalyst that can be used in products worldwide.

The present invention solves this problem by providing an improved transesterification process which involves the addition of a transesterification mixed salt catalyst that is environmentally friendly, can withstand water contents up to 3000 ppm based on total weight of the reaction mixture, and has good performance and reactivity characteristics after the addition of only a single charge of catalyst.

It has been surprisingly discovered that the one-time addition of a single charge of a mixed salt transesterification catalyst results in sufficient (meth)acrylate ester product yields without the necessity of very strict conditions (e.g., low water content and high reactant (meth)acrylate-to-alcohol ratio); thus in turn resulting in increased productivity. Furthermore, the addition of a mixed salt transesterification catalyst provides greater reactor efficiency and/or productivity than achieved by other known methods, and also requires less stringent conditions (for example, the reaction mixture may be dehydrated to a lesser degree) than previous processes.

The present invention relates to a transesterification process, comprising the steps of:
(a) forming a reaction mixture, comprising:
  (1) at least one alkyl(meth)acrylate having Formula I:

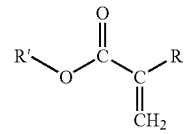

Formula I wherein R=H or $CH_3$; and
wherein R'=$C_1$-$C_8$ straight or branched alkyl;
  (2) at least one alcohol selected from the group consisting of aliphatic linear monoalcohols, branched chain monoalcohols, cycloaliphatic alcohols, aromatic alcohols, functional alcohols, unsaturated alcohols, analiphatic polyols, alcohols of ethylene oxide adduct of ethylene urea, and mixtures thereof; and
  (3) at least one polymerization inhibitor;
(b) adding a mixed salt transesterification catalyst to the reaction mixture;
(c) heating the reaction mixture to commence reaction of the alkyl(meth)acrylate with the at least one alcohol to form a (meth)acrylate ester having Formula II:

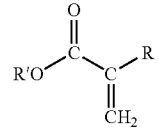

Formula II wherein R=H or $CH_3$, and R'O=an alkoxide of the at least one alcohol, and a product alcohol having Formula III:

 R'—OH

Formula III wherein R'=$C_1$-$C_8$ straight or branched alkyl
(d) removing, by distillation, a mixture of the product alcohol of Formula III and the alkyl(meth)acrylate of Formula I.

In a particular embodiment of the process of the present invention, the adding a mixed salt transesterification catalyst to the reaction is added in only one charge.

In another particular embodiment of the process of the present invention the molar ratio of the at least one alcohol to the at least one alkyl(meth)acrylate is from 1:2 to 1:6.5.

Additionally, the at least one alcohol comprises a hydroxyl alkyl imidazolidine-2-one having Formula IV, as follows:

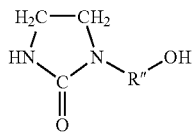

Formula IV wherein R″=$C_1$-$C_8$ straight, branched or cyclic, and saturated or unsaturated, hydrocarbon, and the (meth)acrylate ester product has Formula V, as follows:

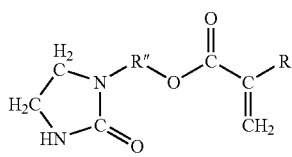

Formula V wherein R=H or $CH_3$, and R″=$C_1$-$C_8$ straight, branched or cyclic, and saturated or unsaturated, hydrocarbon.

In another particular embodiment of the process of the present invention, the hydroxyl alkyl imidazolidine-2-one is hydroxyethyl ethylene urea and the at least one alkyl (meth) acrylate comprises methyl methacrylate.

In another particular embodiment of the process of the present invention, the hydroxyl alkyl imidazolidin-2-one, is for example, hydroxyethyl ethylene urea, and the at least one alkyl(meth)acrylate comprises methyl methacrylate. Moreover, the mixed salt transesterification catalyst comprises a mixture of potassium carbonate and potassium chloride.

In still another embodiment of the process of the present invention, the polymerization inhibitor is selected from the group consisting of oxygen, diethylhydroxylamine, p-methoxy phenol, hydroquinone, phenothiazine, 2,6-dit-butylpara-cresol, 3,5-di-t-butyl-4-hydroxyanisole, 2,5-di-t-butylhydroxyanisole, 4-hydroxy-2,2,6,6-tetramethyl piperidinyl free radical (4-hydroxy-TEMPO), 4-methacryloyloxy-2,2,6,6-tetramethyl piperidinyl free radical, and 4-hydroxy-2,2,6,6-tetramethyl N-hydroxy piperidine and mixtures thereof.

Additionally, the reaction mixture is at a temperature of from 60° C. to 140° C.

The present invention also provides a mixed salt transesterification catalyst comprising at least two salts wherein at least one of the at least two salts is a base.

DETAILED DESCRIPTION OF THE INVENTION

The transesterification process of the present invention produces a (meth)acrylate ester product and involves a first step of forming a reaction mixture which comprises at least one alkyl(meth)acrylate and at least one alcohol, along with a polymerization inhibitor to prevent unwanted polymerization of any meth(acrylate) containing compound.

The at least one alkyl(meth)acrylate has the following Formula I:

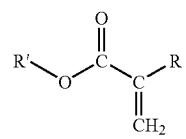

Formula I where R=H or $CH_3$; and where R′=$C_1$-$C_8$ straight or branched alkyl.

Several alcohols are suitable for use in the process of the present invention and include, for example, without limitation: aliphatic linear monoalcohols, branched chain monoalcohols, such as n-butanol, n-propanol, lauryl alcohol, stearyl alcohol, 2-ethylhexanol; cycloaliphatic alcohols, such as cyclophexanol; aromatic alcohols, such as benzyl alcohol; alcohol bearing other functional groups, such as ethylene glycol monomethylether, ethylene glycol monoisopropylether; alcohols of ethylene oxide adduct of ethylene urea, such as hydroxyethyl ethylene urea.

Suitable polymerization inhibitors include oxygen, diethylhydroxylamine, p-methoxy phenol, hydroquinone, phenothiazine, 2,6-di-t-butylpara-cresol, 3,5-di-t-butyl-4-hydroxyanisole, 2,5-di-t-butylhydroxyanisole, 4-hydroxy-2,2,6,6-tetramethyl piperidinyl free radical (4-hydroxy-TEMPO), 4-methacryloyloxy-2,2,6,6-tetramethyl piperidinyl free radical, and 4-hydroxy-2,2,6,6-tetramethyl N-hydroxy piperidine and mixtures thereof. The total amount of polymerization inhibitor added to the reaction mixture ranges typically from lower limits of 10, 100, and 200 to upper limits of 10,000, 5,000, and 3,000 parts per million (ppm). All ranges used herein are inclusive and combinable.

Typically, the amount of alkyl(meth)acrylate reactant in the reaction mixture is in stoichiometric excess of the amount of alcohol reactant. For example, the mole ratio of alcohol to alkyl(meth)acrylate may be typically from 1:1 to 1:20, for example, without limitation, from 1:2 to 1:6.5, or even from 1:2.2 to 1:3.6. This is because, as discussed in further detail hereinafter, a product alcohol is removed, along with a portion of the alkyl(meth)acrylate reactant, from the reaction mixture by distillation during the period of reaction. In one aspect the product alcohol is removed, along with a portion of the alkyl(meth)acrylate reactant, from the reaction mixture by azeotropic distillation. The removed mixture of alkyl(meth)acrylate and product alcohol may be further separated and the alkyl(meth)acrylate reactant may be recycled to the reaction mixture.

In practice, alkyl(meth)acrylates typically contain residual amounts of water or are provided in aqueous solution, to improve their viscosity characteristics and facilitate delivery to the reaction vessel. When the transesterification catalysts to be used are susceptible to deactivation in the presence of water, such as, for example, dibutyl tin oxide and lithium hydroxide catalysts, water should be removed prior to adding the catalyst to the reaction mixture. The mixed salt transesterification catalyst of the present invention does not require water removal from the reaction mixture. These mixed salt transesterification catalysts can tolerate up to 3000 ppm water without hindrance of the catalyst, based on the total weight of the reaction mixture.

If one desires to remove water from the reaction mixture, it is possible, as described hereinabove, to combine the at least one alkyl(meth)acrylate, the at least one alcohol and the polymerization inhibitor, to form a reaction mixture and then remove water from this mixture. Alternatively, it is also possible to combine the at least one alkyl(meth)acrylate and the polymerization inhibitor, remove water therefrom, and then add the at least one alcohol thereto, thus forming the reaction mixture. The step of removing water from the reaction mixture may be accomplished, for example, without limitation, by azoetropic distillation of a mixture of water and alkyl (meth)acrylate.

A further step of the process of the present invention is adding at least one charge of a mixed-salt transesterification catalyst to the reaction mixture. As used herein mixed-salt transesterification catalyst is defined as a combination of at least two salts wherein at least one of the salts is a base. Furthermore one of the salts may be a base while another of the salts may be a modifier salt. Examples of suitable mixed-salt transesterification catalysts of the present invention include at least one basic salt selected from the following without limitation: potassium carbonate, lithium carbonate, cesium carbonate, ammonia carbonate, potassium acetate, potassium phosphate, lithium phosphate, potassium magnesium phosphate, ammonia magnesium phosphate, potassium chlorate, and lithium chlorate; mixed with at least one salt modifier salt selected from the following without limitation: potassium chloride, lithium chloride, cesium chloride, magnesium chloride, zinc chloride, zinc fluoride, cesium, fluoride, potassium fluoride, lithium fluoride, and magnesium fluoride.

In one aspect of the present invention, only one charge of a mixed-salt transesterification catalyst is added. The mixed-salt catalyst charge comprises an amount of transesterification catalyst equal to from 0.1 to 10 mole %, 1-2 mol % based on the total moles of alcohol that are present, or which will be present, in the reaction mixture, depending upon which of the foregoing methods of forming the reaction mixture is practiced. The catalyst can be added by any known, conventional delivery means, such as, without limitation, via a pressurized a pressurized charge hopper, or via a parallel series of individually controlled inline chambers where the catalyst is mixed with the reaction mixture as a carrier, or into a slurry mix with, for example, methyl methacrylate.

If the temperature of the reaction mixture is less than about 60° C. immediately after the charge of the mixed-salt transesterification catalyst has been added, the reaction mixture should be heated to at least 60° C., such as, for example, to at least 90° C., in order to commence the transesterification reaction. Where such heating is necessary, the reaction mixture should be heated within about ten minutes, for example, within five minutes, or even one minute, after addition of the charge of catalyst. This heating should occur at a rate of at least 1° C. per minute, for example, at least 3° C. per minute, until the target temperature is achieved.

As the transesterification reaction proceeds, the products include, but are not necessarily limited to, a product (meth) acrylate and a product alcohol that is different from the reactant alcohol or alcohols that were used to form the reaction mixture. The product (meth)acrylate ester produced by the transesterification process of the present invention has Formula II as follows:

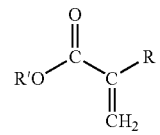

Formula II wherein R=H or CH$_3$, and R'O=an alkoxide of the selected reactant alcohol. The product alcohol has Formula III as follows:

Formula III where R'=C$_1$-C$_8$ straight or branched alkyl.

For example, when the reactant alcohol is hydroxyl alkyl imidazolidin-2-one, having the following Formula IV:

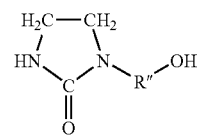

Formula IV wherein R''=C$_1$-C$_8$ straight, branched or cyclic, and saturated or unsaturated, hydrocarbon, then the product (meth) acrylate ester has Formula V as follows:

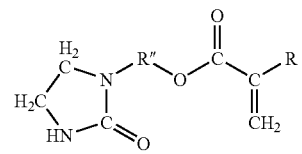

Formula V wherein R=H or CH$_3$, and R''=C$_1$-C$_8$ straight, branched or cyclic, and saturated or unsaturated, hydrocarbon.

The reaction temperature (i.e., the temperature of the reaction mixture during the transesterification reaction) of the process of the present invention may be from about 60° C. to 140° C., for example, without limitation, 70° C., to 125° C., 85-100-. The reaction pressure may be from 760 mm Hg (atmospheric) to reduced or elevated pressures, such as, for example, from 400 mm Hg to 900 mm Hg. 500-760

During the course of the reaction, the product alcohol is removed from the system, by azeotropic distillation, as an azeotropic mixture of the alkyl(meth)acrylate reactant and the product alcohol.

Particular embodiments of the process of the present invention will now be described in detail in connection with the following examples.

EXAMPLES

Example 1

Example 1 demonstrates that a single, one-time charge of mixed-salt transesterification catalyst was capable of producing the desired product, even when the dehydration step for the reduction of water content of the reaction mixture was skipped.

A mixture of 260.3 grams (2.0 moles) of 1-hydroxy ethylene urea (HEEU), 680.8 grams (6.8 moles) of methyl methacrylate (MMA), 1.0 grams (0.006 moles) of 4-hydroxy-2,2, 6,6-tetramethyl piperidinyloxy, free radical (4-hydroxy TEMPO, free radical), 2.77 grams (0.02 moles) of potassium carbonate and 1.49 grams (0.02 moles) of potassium chloride was charged to a 2-liter 4-necked flask equipped with a temperature indicator/controller, magnetic stirrer, mixed gas (8% $O_2$-92% $N_2$) sparge inlet, and a 1 inch diameter-10 plate Oldershaw column fitted with a distillation head, distillate rate removal-vapor pressure temperature controller, and a graduated distillate receiver. The mixture was then heated (at a rate of 2.3° C./min) to 98° C., while the MMA-methanol of reaction azeotrope was removed. During reaction, the mixture was stirred, sparged with mix gas, and continuously heated to reflux at 700mm Hg vacuum while the MMA-methanol of reaction azeotrope was removed. After three hours, the mixture was analyzed by Gas Chromatography (GC) (and for conformation of the results, by High Performance Liquid Chromatography (HPLC) as well) indicating the presence of 36.4% of N-(2-methacryloyloxyethyl)ethylene urea (MEEU), and 3.94% HEEU. The MEEU/HEEU ratio was 9.2, within the desired spec. Upon standing at ambient temperature for two hours, the catalyst was precipitated and was quantitatively recovered by vacuum filtration. Analysis of the filtrate (atomic absorption technique) indicated the presence of less the 20 ppm of chloride.

Example 2

Example 2 demonstrates the reuse of the spent recovered catalyst in subsequent reactions.

A mixture of 260.3 grams (2.0 moles) of 1-hydroxy ethylene urea (HEEU), 680.8 grams (6.8 moles) of methyl methacrylate (MMA), 1.0 grams (0.006 moles) of 4-hydroxy-2,2,6,6-tetramethyl piperidinyloxy, free radical (4-hydroxy TEMPO, free radical), 2.77 grams (0.02 moles) of potassium carbonate and 1.49 grams (0.02 moles) of potassium chloride was charged to a 2-liter 4-necked flask equipped with a temperature indicator/controller, magnetic stirrer, mixed gas (8% $O_2$-92% $N_2$) sparge inlet, and a 1 inch diameter-10 plate Oldershaw column fitted with a distillation head, distillate rate removal-vapor pressure temperature controller, and a graduated distillate receiver. The mixture was then heated (at a rate of 2.3° C./min) to 98° C., while removing the MMA-methanol of reaction azeotrope. During reaction, the mixture was stirred, sparged with mix gas, and continuously heated to reflux at 700 mm Hg vacuum while removing the MMA-methanol of reaction azeotrope. After three hours, the mixture was analyzed by GC (and by HPLC) revealing identical composition to the previous example. Upon standing at ambient temperature, the mixed-salts precipitated out and were removed by vacuum filtration.

Example 3

Example 3 demonstrates how the aforementioned heterogeneous catalytic system produced MEEU at a lower ratio of MMA to HEEU (3.2:1).

A mixture of 260.3 grams (2.0 moles) of 1-hydroxy ethylene urea (HEEU), 640.5 grams (6.4 moles) of methyl methacrylate (MMA), 1.0 grams (0.006 moles) of 4-hydroxy-2,2,6,6-tetramethyl piperidinyloxy, free radical (4-hydroxy TEMPO, free radical) was charged to a 2-liter 4-necked flask equipped with a temperature indicator/controller, magnetic stirrer, mixed gas (8% $O_2$-92% $N_2$) sparge inlet, and a 1 inch diameter-10 plate Oldershaw column fitted with a distillation head, distillate rate removal-vapor pressure temperature controller, and a graduated distillate receiver. The mixture was then heated (at a rate of 2.3° C./min) to 98° C., while the MMA-methanol of reaction azeotrope was removed. During reaction, the mixture was stirred, sparged with mix gas, and continuously heated to reflux at 700 mm Hg vacuum while MMA-methanol of reaction azeotrope was removed. After one hour of reaction, methanol generation slowed, as evident by column temperatures. In order to increase the rate of methanol removal, the vacuum was gradually reduced from 700mm Hg to 500 mm Hg over the course of the reaction. Three hours later the reaction was considered complete. At this point the mixture contained 36% MEEU and a residue of 2.43% HEEU.

Example 4

Example 4 demonstrates that other mixed-salts combinations such as $Cs_2CO_3$—LiCl, were successfully employed in MEEU production. The $Cs_2CO_3$—LiCl mixture exhibited high activity even at relatively low temperature ranges (90° C.-95° C.). At this temperature range, other catalysts, traditionally used for the preparation of this monomer (such as LiOH and DBTO), exhibit low activity.

A mixture of 260.3 grams (2.0 moles) of 1-hydroxy ethylene urea (HEEU), 680.8 grams (6.8 moles) of methyl methacrylate (MMA), 1.0 grams (0.006 moles) of 4-hydroxy-2,2,6,6-tetramethyl piperidinyloxy, free radical (4-hydroxy TEMPO, free radical), 3.26 grams (0.01 moles) of cesium carbonate and 1.64 grams (0.04 moles) of lithium chloride was charged to a 2-liter 4-necked flask equipped with a temperature indicator/controller, magnetic stirrer, mixed gas (8% $O_2$-92% $N_2$) sparge inlet, and a 1 inch diameter-10 plate Oldershaw column fitted with a distillation head, distillate rate removal-vapor pressure temperature controller, and a graduated distillate receiver. The mixture was then heated (at a rate of 2.3° C./min) to 98° C., while removing the MMA-methanol of reaction azeotrope. During reaction the mixture was stirred, sparged with mix gas, and continuously heated to reflux at 700 mm Hg vacuum while removing the MMA-methanol of reaction azeotrope. After three hours, the mixture was analyzed by GC (and for conformation of the results, by HPLC as well) indicating the presence of 42.3% of N-(2-methacryloyloxyethyl)ethylene urea (MEEU), and 2.88% HEEU. The MEEU/HEEU ratio was 14.7, well within the desired spec. Upon standing at ambient temperature for two hours, the catalyst was precipitated out and was recovered quantitatively by vacuum filtration. Analysis of the filtrate (atomic absorption technique) indicates the presence of less the 20 ppm of chloride.

Table I below exemplifies the processes in Examples 1-4 with ratios of MMA to HEEU of 3.4:1.

TABLE I

Six Mixed-salts Combinations in MEEU Production (3 hr, 98° C., MMA to HEEU ratio = 3.4:1)

| Catalysts | Mole ratio | % MEEU | % HEEU | MEEU/HEEU |
|---|---|---|---|---|
| $Li_2CO_3$/LiCl | 1:1 | 27.7 | 15.6 | 1.8 |
| $Li_2CO_3$/CsCl | 1:1 | 10.7 | 14.4 | 0.7 |
| $K_2CO_3$/KCl | 1:1 | 36.4 | 3.9 | 9.2 |
| $Cs_2CO_3$/CsCl* | 1:1 | 11.1 | 1.9 | 6.0 |
| $Cs_2CO_3$/LiCl | 1:1 | 32.0 | 3.1 | 10.2 |
| $Cs_2CO_3$/LiCl | 0.5:2 | 42.3 | 2.9 | 14.7 |

*Strong base/nuceleophilic promoting 1,4-conjugate addition resulting in Michael products Select catalysts such as $K_2CO_3$—KCl or $Cs_2CO_3$—LiCL, were amenable for the preparation of MEEU. These heterogeneous catalyst systems produced MEEU at a very rapid pace, significantly faster than lithium hydroxide monohydrate. While DBTO and the mixed salt catalyst had relatively the same performance characteristics, the lithium hydroxide catalyst required significantly more charges to produce less comparable results. These results are exemplified in Table II.

TABLE II

| | Performance of three catalyst systems at 3.2:1 MMA:HEEU molar ratio | | | |
|---|---|---|---|---|
| Catalyst | Time (hr.) | T° C./mmHg | MEEU/ HEEU | # of charges of catalysts |
| DBTO comparative | 4 | 98/700 (1 hr.) | 21.6 | 1 |
| LiOH•H₂O comparative | 4 | 115/700 | 7.91 | 5 |
| K₂CO₃—KCl | 4 | 98/700-550 | 22.6 | 1 |

It will be understood that the embodiments of the present invention described hereinabove are merely exemplary and that a person skilled in the art may make variations and modifications without departing from the spirit and scope of the invention. All such variations and modifications are intended to be included within the scope of the present invention.

We claim:

1. A transesterification process, comprising the steps of:
    (a) forming a reaction mixture, comprising:
        (i) at least one alkyl (meth)acrylate having Formula I:

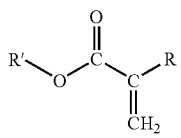

Formula I wherein H=H or CH3; and
wherein R'=$C_1$-$C_8$ straight or branched alkyl;
    (2) at least one alcohol selected from the group consisting of aliphatic linear monoalcohols, branched chain monoalcohols, cycloaliphatic alcohols, aromatic alcohols, functional alcohols, unsaturated alcohols, analiphatic polyols, alcohols of ethylene oxide adduct of ethylene urea, and mixtures thereof; and
    (3) at least one polymerization inhibitor;
(b) adding a heterogeneous mixed salt transesterification catalyst to the reaction mixture;
wherein the mixed salt catalyst comprises at least one base and at least one modifier salt selected from the group consiting of potassium chloride, lithium chloride, cesium chloride. magnesium chloride, zinc chloride, zinc fluoride, cesium, fluoride, potassium fluoride, lithium fluoride, and magnesium fluoride;
(c) heating the reaction mixture to commence reaction of the alkyl (meth)acrylate with the at least one alcohol to form a (meth)acrylate ester having Formula II:

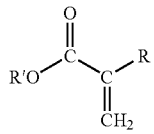

Formula II wherein R=H or $CH_3$, and R'O=an alkoxide of the at least one alcohol, and
a product alcohol having Formula III:

 R'—OH

Formula III wherein R'=$C_1$-$C_8$ straight or wherein R'=$C_1$-$C_8$ straight or branched alkyl; and
    (d) removing, by distillation, a mixture of Formula III and Formula I.

2. The transesterification process according to claim 1, wherein the adding a mixed salt transesterification catalyst to the reaction mixture is added in only one charge.

3. The transesterification process according to claim 1, wherein the molar ratio of the at least one alcohol to the at least one alkyl (meth)acrylate is from 1:2 to 1:6.5.

4. The transesterification process according to claim 1, wherein the at least one alcohol comprises a hydroxyl alkyl imidazolidine-2-one having Formula IV, as follows:

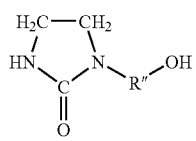

Formula IV wherein R"=$C_1$-$C_8$ straight, branched or cyclic, and saturated or unsaturated, hydrocarbon, and the (meth)acrylate ester roduct has Formula V, as follows:

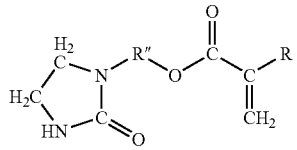

Formula V wherein R=H or $CH_3$, and R"=$C_1$-$C_8$ straight branched or cyclic, and saturated or unsaturated, hydrocarbon.

5. The transesterification process according to claim 4, wherein the hydroxyl alkyl imidazolidine-2-one is hydroxyethyl ethylene urea and the at least one alkyl (meth)acrylate comprises methyl methacrylate.

6. The transesterification process according to claim 1, wherein the mixed salt transesterification catalyst comprises a mixture of potassium carbonate and potassium chloride.

7. The transesterification process according to claim 1, wherein the mixed salt transesterification catalyst comprises at least two salts wherein at least one of the at least two salts is a salt selected from the group consisting of potassium carbonate, lithium carbonate, cesium carbonate, ammonia carbonate, potassium acetate, potassium phosphate, lithium phosphate, potassium magnesium phosphate, ammonia magnesium phosphate, potassium chlorate, and lithium chlorate; and at least one other of the at two salts is a salt selected from the group consisting of potassium chloride, lithium chloride, cesium chloride, magnesium chloride, zinc chloride, zinc fluoride, cesium, fluoride, potassium fluoride, lithium fluoride, and magnesium fluoride.

8. The transesterification process according to claim 1, wherein the polymerization inhibitor is selected from the group consisting of oxygen, diethyihydroxylamine, p-methoxy phenol, hydroquinone, phenothiazine, 2,6-dit-butylparacresol, 3,5-di-t-butyl- 4hydroxyanisole, 2,5-di-t-butylhydroxyanisole, 4-hydroxy- 2,2,6,6-tetramethyl piperidinyl free radical (4 hydroxy-TEMPO), 4-methacryloyloxy- 2,2,6, 6-tramethyl piperidinyl free radical, and 4-hydroxy-2,2,6,6-tetramethyl N-hydroxy piperidine and mixtures thereof.

9. The transesterification process according to claim 1, further comprising the step of maintaining the reaction mixture at a temperature of from 60° C. to 140° C.

* * * * *